United States Patent
Yamazaki (10) Patent No.: US 9,630,125 B2
(45) Date of Patent: Apr. 25, 2017

(54) GAS-BLOWING LIQUID SAMPLE INFUSING DEVICE AND INFUSION CONTAINER USED FOR THE SAME

(71) Applicant: SHIMADZU CORPORATION, Kyoto-shi, Kyoto (JP)

(72) Inventor: Tomoyuki Yamazaki, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 96 days.

(21) Appl. No.: 14/732,856

(22) Filed: Jun. 8, 2015

(65) Prior Publication Data

US 2016/0354709 A1   Dec. 8, 2016

(51) Int. Cl.
*B01F 3/04* (2006.01)
*B01D 15/14* (2006.01)

(52) U.S. Cl.
CPC .......... *B01D 15/14* (2013.01); *B01F 3/04021* (2013.01)

(58) Field of Classification Search
CPC ................ B01D 15/14; B01F 3/04021
USPC ................................... 261/76, 78.2
See application file for complete search history.

(56) References Cited

U.S. PATENT DOCUMENTS

| 2003/0155436 A1* | 8/2003 | Nilsen ............... B01D 53/1462 239/427 |
| 2015/0174006 A1* | 6/2015 | Qiu .......................... A61J 1/10 604/413 |

FOREIGN PATENT DOCUMENTS

| JP | 2003-149217 A | 5/2003 |
| WO | 2009/044425 A1 | 4/2009 |
| WO | 2009/044426 A1 | 4/2009 |
| WO | 2009/044427 A1 | 4/2009 |
| WO | 2009/044428 A1 | 4/2009 |

* cited by examiner

*Primary Examiner* — Charles Bushey
(74) *Attorney, Agent, or Firm* — Sughrue Mion, PLLC (57) ABSTRACT

A gas-blowing liquid sample infusing device includes a sample introducing tube 17 made from a liquid-sample inner tube 40 and a nebulizing-gas outer tube 41 for nebulizing and supplying a liquid sample, and an exhaust sealing tube 18 provided on the circumference of the sample introducing tube 17, and a cushion member 43 that is mounted on the opening of a sample container 19 (the body of an infusion container 21), that allows the sample introducing tube 17 to pass through and has a contact surface for contacting the lower end of the exhaust sealing tube 18, and an engaging member (lid) 20 that includes a cushion admitting concave part 42 in which an engaging part 44 that is mounted on the opening of the sample container 19 and prevents the upward movement of the cushion member 43 is provided on the lateral surface of the inner circumference.

10 Claims, 5 Drawing Sheets

AS EXHAUST SEALING TUBE IS MOVED DOWNWARD, CUSHION IS FIRMLY ENGAGED BY MEANS OF ENGAGING PART FROM INNER SIDE TO OUTER SIDE OF HOLE

AS EXHAUST SEALING TUBE IS MOVED DOWNWARD, CUSHION IS FIRMLY ENGAGED BY MEANS OF ENGAGING PART FROM INNER SIDE TO OUTER SIDE OF HOLE

GAS-BLOWING LIQUID SAMPLE INFUSING DEVICE AND INFUSION CONTAINER USED FOR THE SAME

TECHNICAL FIELD

The present invention relates to a gas-blowing liquid sample infusing device for infusing a liquid sample into an infusion container while blowing gas to the liquid sample, thereby nebulizing the liquid sample, and the infusion container used for the same. The gas-blowing liquid sample infusing device and the infusion container can be suitably used in a preparative separation-purification device for separating one or a plurality of components contained in a solution by use of a liquid chromatograph and subsequently purifying and collecting each component.

BACKGROUND ART

For example, in pharmaceuticals or similar fields, the collection of samples stored in the form of library is made by means of preparative separation-purification devices in which a liquid chromatograph is utilized. In a device disclosed in Patent Literature 1, target components (compounds) in a sample solution are temporally separated by the liquid chromatograph and introduced into trap columns respectively prepared for the target components, and temporarily held in the trap columns. Subsequently, a solvent is flown into each trap column to elute the target component captured in the trap column, thereby collecting a solution, which contains the target component, in a container. Then, a drying process is applied to the solution collected, in which the solvent is eliminated and the target component is collected as a solid body.

The drying process is normally performed by heating the solution collected. However, since the temperature of the target component cannot be raised too high in order to avoid change in quality of the target component, some components require several hours to one day in this method. In the preparative separation-purification process, the drying process takes the longest time, and therefore it is essential to reduce the time of the drying process in order to reduce the whole time of the process.

In order to solve the above-mentioned problem, Patent Literatures 2 to 5 disclose a method in which a solution containing a target component is dropped in a collection container with a blow of air or gas, such as nitrogen, to nebulize the solution, thereby the vaporization of the solvent is enhanced.

Figure 7A:
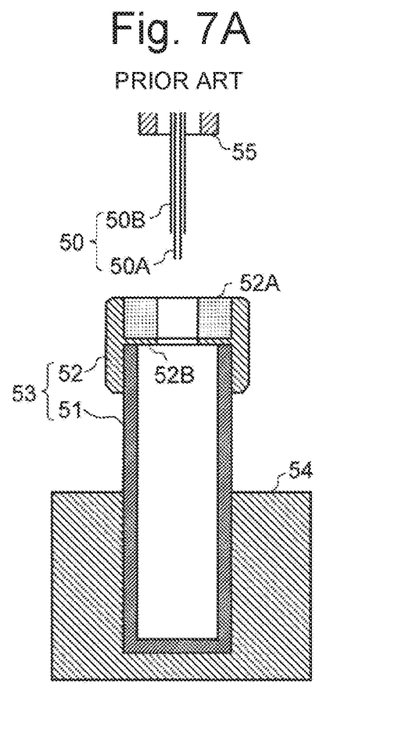
FIGS. 7A to 7D are descriptive diagrams of the powdering process of a conventional preparative separation-purification device.

A general procedure for the drying process (hereinafter referred to as "gas-blowing vaporizing and drying process") according to the method of Patent Literatures 2 to 5 will be described referring to FIGS. 7A, 7B, 7C and 7D. A preparative separation-purification device in FIGS. 7A to 7D includes a temperature adjusting block 54 that heats a collection container 53 to a predetermined temperature, a solution-introducing tube 50 that introduces the solution to the collection container 53 embedded in the temperature adjusting block 54, and a sealing tube 55 that discharges nebulizing gas introduced in the collection container 53 and a solvent vaporized in the collection container 53 from the collection container 53 while preventing their leak to the surroundings of the collection container 53. The solution-introducing tube 50 and the sealing tube 55 are integrally formed, and the solution-introducing tube 50 has a double tube structure made from an inner tube 50A through which the solution flows and an outer tube 50B through which the nebulizing gas flows. The collection container 53 includes a container body 51, and a lid 52 that can fit on the opening of the upper part of container body 51. The lid 52 includes a doughnut-shaped cushion 52A and a cushion mounting part 52B, having a hole in the center, on which the cushion 52A is mounted (FIG. 7A).

Figure 7B:
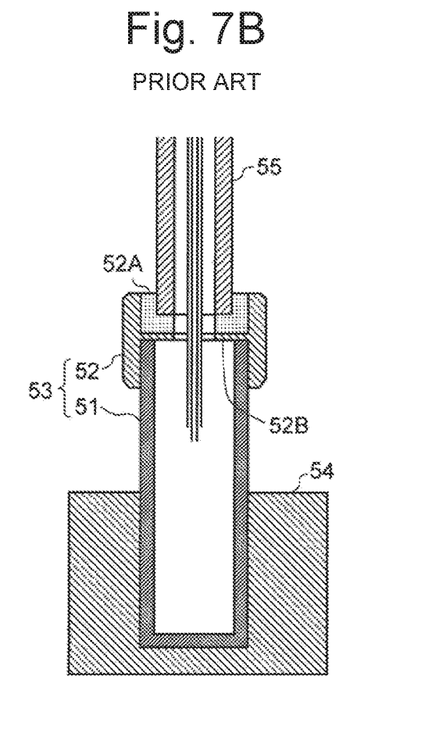
Figure 7C:
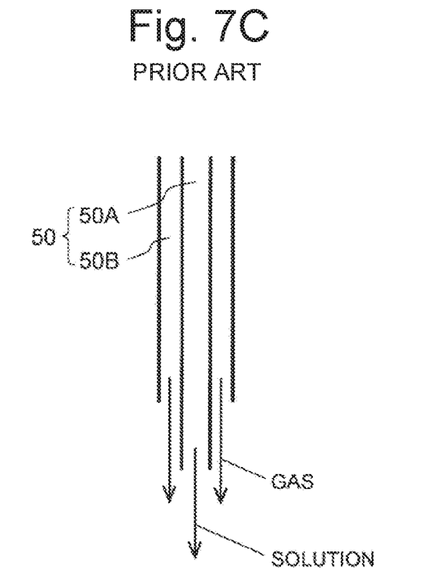

In the gas-blowing vaporizing and drying process, the solution-introducing tube 50 descends and passes through the cushion 52A and the hole in the center of the cushion mounting part 52B, and is inserted into the collection container 53 (FIG. 7B). The sealing tube 55 also descends along with the solution-introducing tube 50, and the end of the sealing tube 55 presses the cushion 52A. Accordingly, the end of the sealing tube 55 is tightly contacts the cushion 52A, and the collection container 53 and the sealing tube 55 are hermetically sealed with each other. Subsequently, the solution is delivered to the inner tube 50A, and the nebulizing gas is delivered to the outer tube 50B (FIG. 7C). Consequently, the solution dropped from the end of the inner tube 50A is sheared by the flow of the nebulizing gas from the outer tube 50B, and is turned to fine droplets (mist), which attach to the inner wall of the collection container 53. The collection container 53 is heated in advance by the temperature adjusting block 54, so that the solvent in fine droplets attached to the inner wall vaporizes, and the target component (solute) is left there in the form of powder. The nebulizing gas introduced in the collection container 53 and the solvent vaporized in the collection container 53 are discharged through the sealing tube 55 to the outside.

CITATION LIST

Patent Literature

[Patent Literature 1] JP 2003-149217 A
[Patent Literature 2] WO2009/044425
[Patent Literature 3] WO2009/044426
[Patent Literature 4] WO2009/044427
[Patent Literature 5] WO2009/044428

SUMMARY OF INVENTION

Technical Problem

Figure 7D:
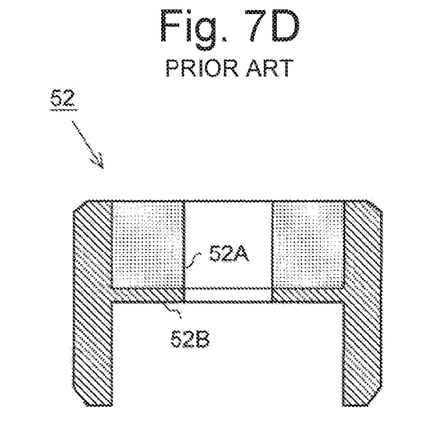

Regarding the preparative separation-purification device illustrated in FIGS. 7A to 7D, while the collection container 53 is repeatedly used, plastic deformation occurs in the cushion 52A, and the end of the sealing tube 55 will not be appropriately sealed. In view of such a case, it is designed so that the cushion 52A is simply put on the cushion mounting part 52B in order to enable easy replace of the cushion 52A (FIG. 7D).

However, in such a design of the lid 52, after the completion of the process described above, the cushion 52A that has deformed adheres to the end of the sealing tube 55, comes off from the cushion mounting part 52B and is pulled up together with the sealing tube 55. Accordingly, when the gas-blowing vaporizing and drying process is carried out with respect to the next collection container, the cushion 52A adhered to the end of the sealing tube 55 prevents the next collection container from being appropriately sealed, which causes troubles such as the leakage of the nebulizing gas introduced in the collection container and the solvent vaporized in the collection container.

In order to solve the aforementioned problems, it is an object of the present invention to provide an infusion container and a gas-blowing liquid sample infusing device, which can be steadily sealed in such a manner as not to leak the nebulizing gas introduced in the infusion container and the solvent vaporized in the infusion container, even when processes for infusing the liquid sample into a predetermined container (hereinafter referred to as "infusion container") and concurrently blowing gas to the liquid sample, thereby nebulizing the liquid sample, are consecutively carried out, as represented in the aforementioned gas-blowing vaporizing and drying process.

Solution to Problem

One aspect of the present invention that has been achieved in order to solve the aforementioned problems is an infusion container used for a gas-blowing liquid sample infusing device which includes a sample introducing tube for nebulizing and supplying a liquid sample and an exhaust sealing tube provided on a circumference of the sample introducing tube, where the sample introducing tube is made from a liquid-sample inner tube and a nebulizing-gas outer tube, the infusion container including:

(a) a container body having an opening on an upper part,
(b) a lid configured to be mounted on the opening,
(c) a cushion admitting concave part provided in the lid and having an opening on an upper part and a hole for allowing the sample introducing tube to pass though on a bottom part,
(d) an annular cushion member configured to be admitted in the cushion admitting concave part, the annular cushion member having a contact surface for contacting a lower end of the exhaust sealing tube, and
(e) an engaging part provided on a surface of an inner circumference of the cushion admitting concave part and configured to prevent an upward movement of the cushion member.

Regarding the infusion container of the gas-blowing liquid sample infusing device according to the present invention, the engaging part that prevents the upward movement of the cushion member is provided, so that the cushion member is prevented from being moved upward together with the exhaust sealing tube. Accordingly, even when the processes such as the gas-blowing vaporizing and drying process are consecutively carried out, the end of the exhaust sealing tube is steadily pressed against the cushion member, thereby sealing the space therebetween, so that the nebulizing gas or the vaporized solvent can be prevented from leaking from the space between the exhaust sealing tube and the cushion member. Further, the cushion member is merely engaged by the engaging part, so that the cushion member can be easily replaced as in the conventional manner.

It is a normal practice, especially when collecting samples of pharmaceuticals, to avoid the use of adhesives because intrusion of even a small amount of such impurity substances in the container is harmful. Accordingly, the infusion container that engages the cushion member without using adhesives is suitable for a preparative separation-purification device that is used for a wide range of uses such as the collection of the samples of pharmaceuticals and the aforementioned use.

The engaging part may be, for example, made from screw-threads formed on the surface of the inner circumference. Otherwise it may be barbs or projections/depressions provided on the surface of the inner circumference.

Another aspect of the present invention that has been achieved in order to solve the aforementioned problems is a gas-blowing liquid sample infusing device that nebulizes and supplies a liquid sample to an interior of a sample container that having an opening on an upper part, the gas-blowing liquid sample infusing device including:

(a) a sample introducing tube made from a liquid-sample inner tube that supplies the liquid sample and a nebulizing gas outer tube that supplies gas for nebulizing the liquid sample, (b) an exhaust sealing tube provided on a circumference of the sample introducing tube, (c) an annular cushion member configured to be mounted on the opening, the annular cushion member having a through hole for allowing the sample introducing tube to pass through and a contact surface for contacting a lower end of the exhaust sealing tube, and (d) an engaging member configured to be mounted on the opening and configured to prevent an upward movement of the cushion member in a state where the cushion member is mounted on the opening.

Preferably, the engaging member is a lid of the sample container, and the lid includes a cushion admitting concave part configured to be a concave part that admits the cushion member and configured to include an engaging part, which prevents the upward movement of the cushion member, provided on a surface of an inner circumference of the cushion admitting concave part.

Preferably, a tapered pointed part is provided at an end of the exhaust sealing tube, and an external diameter of the thinnest portion of the tapered pointed part is equal to or less than a diameter of the through hole, and an external diameter of the thickest portion of the tapered pointed part is larger than the diameter of the through hole.

With this constitution, as the exhaust sealing tube moves downward, the cushion member is deformed in an obliquely downward direction, and in this time, the cushion member is inserted into the engaging part provided on the surface of the inner circumference of the cushion admitting concave part. Accordingly, the resistance to the movement of the cushion member in the vertical direction is further increased, and when the exhaust sealing tube moves upward, the cushion member is steadily prevented from being slipped out of the cushion admitting concave part.

Advantageous Effects of the Invention

In the infusion container according to the present invention, the upward movement of the cushion member is prevented by the engaging part provided on the surface of the inner circumference of the cushion admitting concave part. Furthermore, in the gas-blowing liquid sample infusing device according to the present invention, the upward movement of the cushion member is prevented by the engaging member. Accordingly, as represented in the aforementioned gas-blowing vaporizing and drying process, even when processes for infusing the liquid sample into the infusion container and concurrently blowing gas to the liquid sample, thereby nebulizing the liquid sample, are consecutively carried out, the end of the exhaust sealing tube is steadily pressed against the cushion member, thereby sealing the space therebetween, so that the nebulizing gas or the vaporized solvent can be prevented from leaking from the space between the exhaust sealing tube and the cushion member. Further, the cushion member is merely locked by the engaging part (the engaging member), so that the cushion member can be easily replaced as in the conventional manner.

BRIEF DESCRIPTION OF DRAWINGS

FIG. 1 is a configuration diagram of a main part of a preparative separation-purification device to which a gas-blowing liquid sample infusing device according to an embodiment of the present invention is applied.

FIGS. 2A and 2B are schematic longitudinal cross-sectional diagrams of an infusion container used in the gas-blowing liquid sample infusing device of the present embodiment.

FIGS. 4A and 4B are schematic longitudinal cross-sectional diagrams illustrating the modified example of the exhaust sealing tube used in the gas-blowing liquid sample infusing device of the present embodiment.

DESCRIPTION OF EMBODIMENTS

Figure 1:
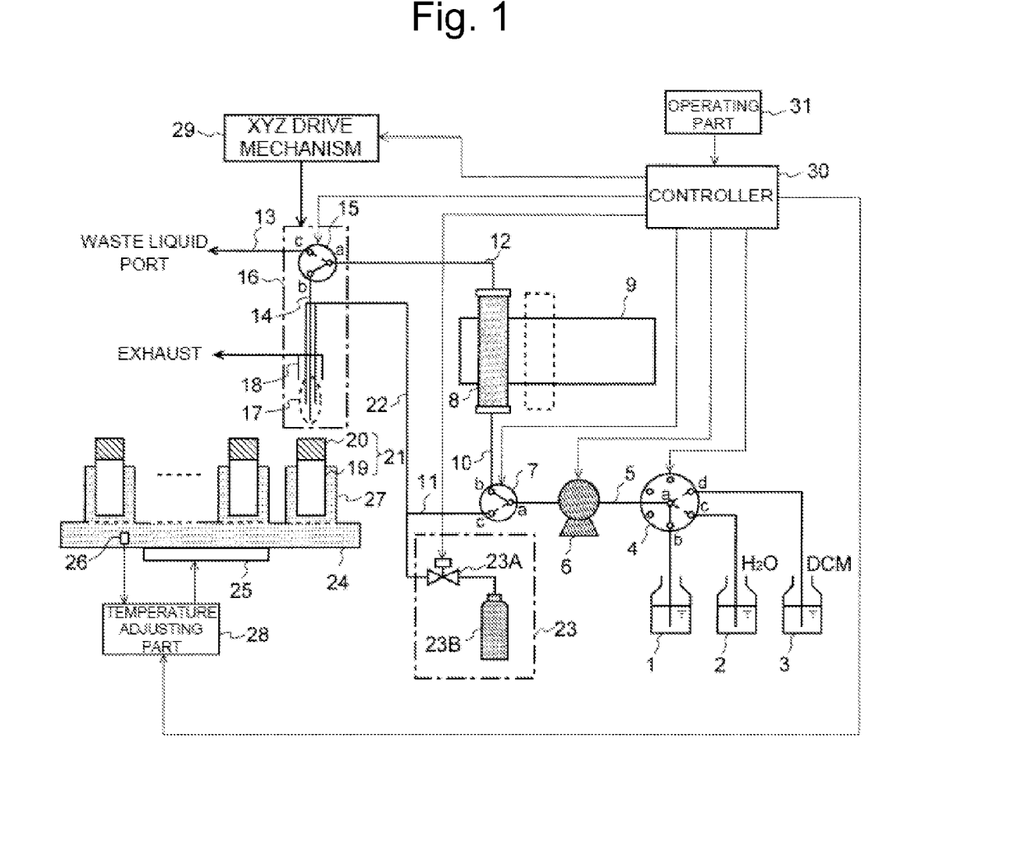

An embodiment of a gas-blowing liquid sample infusing device according to the present invention will be described referring to FIG. 1, FIGS. 2A and 2B, and FIGS. 3A and 3B. FIG. 1 is a configuration diagram of a main part of a preparative separation-purification device to which the gas-blowing liquid sample infusing device of the present embodiment is applied. As described later, the preparative separation-purification device is configured to fractionate in advance the solution that contains a target component, by means of a preparative liquid chromatograph not illustrated, but the configuration may be applied in which the preparative liquid chromatograph is directly connected to the preparative separation-purification device, and the solution fractionated by the preparative liquid chromatograph is directly introduced to the preparative separation-purification device.

Figures 2A, 2B:
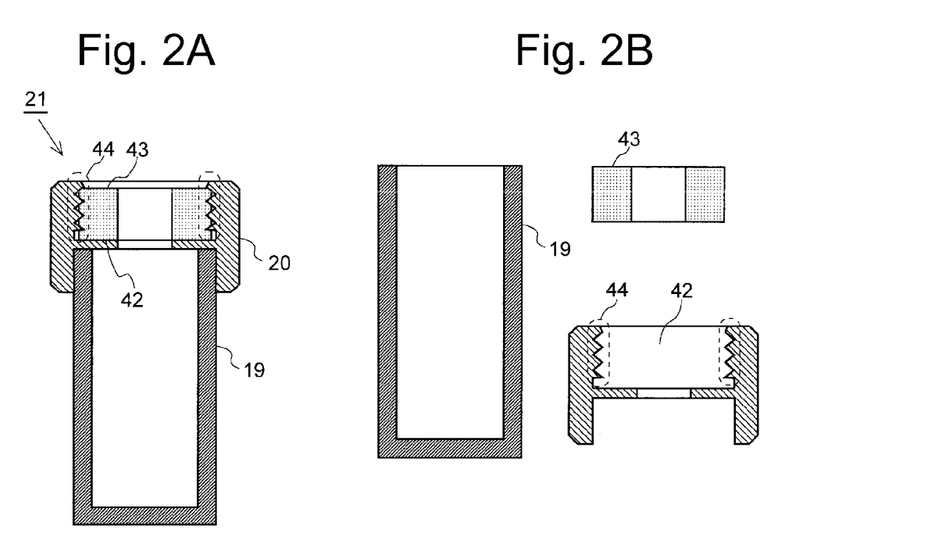
FIG. 2A is an overall view of the infusion container.
FIG. 2B is a diagram illustrating respective components constituting the infusion container.
Figure 3A:
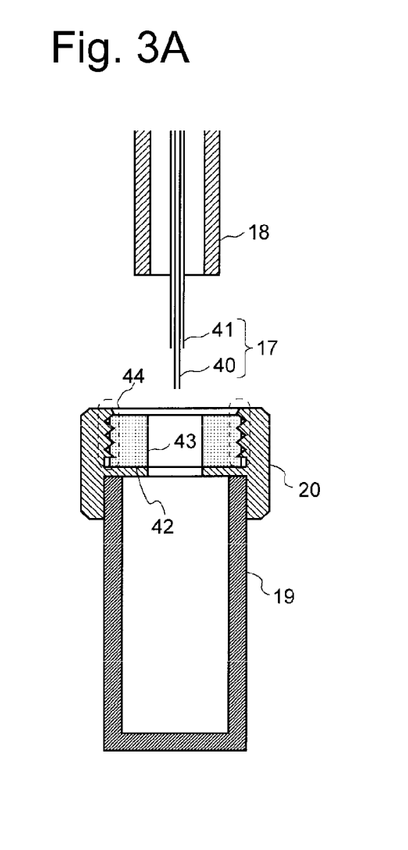
FIG. 3A is a schematic longitudinal cross-sectional diagram illustrating a state before a sample introducing tube is inserted into the infusion container.
Figure 3B:
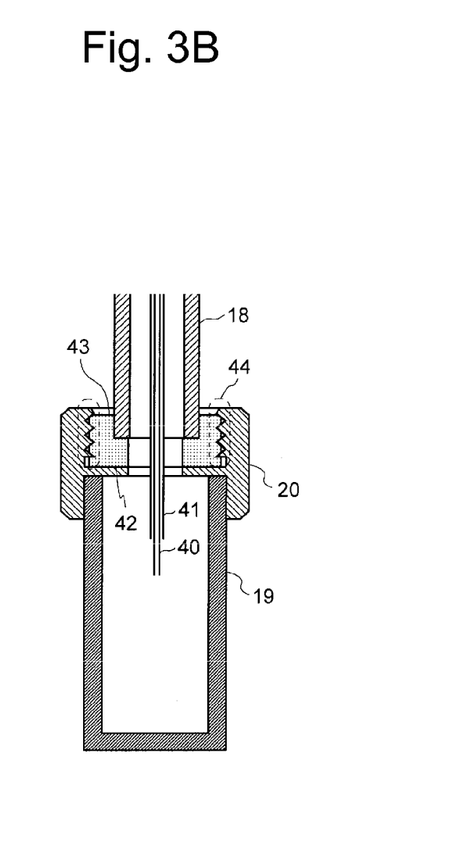
FIG. 3B is a schematic longitudinal cross-sectional diagram illustrating a state after the sample introducing tube is inserted into the infusion container, with regard to the gas-blowing liquid sample infusing device of the present embodiment.

FIGS. 2A and 2B are schematic longitudinal cross-sectional diagrams of an infusion container used in the gas-blowing liquid sample infusing device of the present embodiment. FIGS. 3A and 3B are schematic longitudinal cross-sectional diagrams illustrating states before and after a sample introducing tube is inserted into the infusion container with regard to the gas-blowing liquid sample infusing device of the present embodiment.

In FIG. 1, a solution container 1 admits a solution fractionated in advance, which contains a target component, and a solvent in the solution is mainly made from the mobile phase used in the preparative liquid chromatograph. A pure water container 2 admits pure water ($H_2O$), and an eluting solvent container 3 admits dichloromethane (DCM). A switching valve 4 switches passages to selectively flow any one of liquids admitted in the three containers 1, 2, and 3 toward a passage 5. A liquid-delivery pump 6 that draws and delivers the liquid at a predetermined flow rate is provided in the passage 5.

The outlet end of the passage 5 is connected to the port a of a switching valve 7. A passage 10 leading to a trap column 8 filled with absorbents to capture the target component is connected to the port b of the switching valve 7, and a passage 11 leading to a later-described passage 22 for nebulized gas is connected to the port c of the switching valve 7. The switching valve 7 selectively connects the passage 5 to either the passage 10 or the passage 11.

The trap column 8 is erected and held approximately vertically by means of a column rack 9, in a way that an inlet end connected to the passage 10 is oriented straight downward and that an outlet end connected to a later-described passage 12 is oriented upward. Although only one trap column 8 is illustrated in FIG. 1, a plurality of trap columns 8 may be arranged side by side and held by the column rack 9 as illustrated in a dotted line in FIG. 1.

The other end of the passage 12, whose one end is connected to the outlet end of the trap column 8, is connected to the port a of a switching valve 15 incorporated in a fractional head 16, and a passage 14 is connected to the port b of the switching valve 15, and a passage 13 leading to a waste liquid port is connected to the port c of the switching valve 15. The switching valve 15 selectively connects the passage 12 to either the passage 13 or the passage 14.

The fractional head 16 includes a sample introducing tube 17 and an exhaust sealing tube 18 integrally provided on the outer side of the sample introducing tube 17, and the fractional head 16 can be vertically and horizontally moved by an XYZ drive mechanism 29 constituted by a plurality of motors and the like. The sample introducing tube 17 includes an inner tube 40 connected to the passage 14 and an outer tube 41 connected to the passage 22 (it is noted that FIG. 1 is a schematic diagram illustrating the sample introducing tube 17 and an infusion container 21, and the specific configuration is illustrated in FIGS. 3A and 3B). As described later, the solution that contains the target component is delivered to the inner tube 40 through the passage 14, and the nebulizing gas is delivered to the outer tube 41 through the passage 22.

Infusion containers 21, in which the solution is infused, are individually stored in a temperature adjusting block 27 of a container rack 24 in which a heater 25 and a temperature sensor 26 such as a thermistor are mounted. The container rack 24 and the temperature adjusting block 27 of the container rack 24 are formed of, for example, materials having favorable thermal conductivity, such as aluminum, and the exteriors thereof are covered by heat insulating materials (not illustrated) in order to prevent heat from leaking out to the surroundings.

At least the bottom part of each infusion container 21 is brought into contact with the upper surface of the temperature adjusting block 27 in order to facilitate the conduction of heat from the temperature adjusting block 27. As a more favorable form, the lateral circumferential surface of each infusion container 21 may be configured to come in contact with the inner circumferential surface of the temperature adjusting block 27. A temperature adjusting part 28 provided separately from the container rack 24 adjusts a heating current supplied to the heater 25 so that a monitor temperature detected by the temperature sensor 26 reaches a target temperature. Accordingly, the infusion containers 21 are heated and maintained appropriately at a constant temperature.

Each infusion container 21 includes an infusion container body 19 and a lid 20 fitted on the opening of the upper part thereof. The lid 20 includes a cushion admitting concave part 42 that includes a hole, through which the sample introducing tube 17 is introduced to the interior of the infusion container body 19, provided in the center thereof. A doughnut-shaped cushion (annular cushion member) 43 is stored in the cushion admitting concave part 42. Screw-threads, which represent the characteristic structure of the present invention, are formed as an engaging part 44 on the lateral surface of the inner circumference of the cushion admitting concave part 42. The cushion 43 is pressed into the engaging part 44 in such a manner that the lateral surface of the outer circumference of the cushion 43 is engaged with the engaging part 44, and the cushion 43 is tightly fitted in the cushion admitting concave part 42. It is noted that the infusion container body 19 corresponds to the sample container that supplies the liquid sample by use of the liquid sample infusing device according to the present invention. The lid 20 corresponds to an engaging member in the liquid sample infusing device according to the present invention.

The fractional head 16 is transferred by the XYZ drive mechanism 29 over an arbitrary container from among a plurality of infusion containers 21 stored in the container rack 24, and then moved down. This allows the sample introducing tube 17 to be introduced into the interior of the infusion container body 19 through the cushion admitting concave part 42 and the hole in the center of the cushion 43. The end of the exhaust sealing tube 18 presses the upper surface (contact surface) of the cushion 43, thereby hermetically sealing space between the exhaust sealing tube 18 and the infusion container 21. In this state, a later-described gas-blowing vaporizing and drying process is carried out.

The container rack 24 may be configured to be transferred instead of the fractional head 16 being transferred.

A gas supply part 23 includes a proportional valve 23A and a gas cylinder 23B and delivers the nebulizing gas to the outer tube 41 of the sample introducing tube 17 through the passage 22.

A controller 30 inclusive of a CPU and the like executes control of the switching operation of the switching valves 4, 7, and 15, the operations (flow rate or flow velocity) of the liquid-delivery pump 6 and the gas supply part 23, the settings for the target temperature of the temperature adjusting part 28, and the transfer of the fractional head 16 via the XYZ drive mechanism 29 in accordance with programs set in advance, thereby automatically performing the preparative separation-purification operation. An operating part 31 is used for inputting and setting the conditions of the preparative separation-purification operation.

Subsequently, the procedure of the gas-blowing vaporizing and drying process performed by the preparative separation-purification device in FIG. 1 will be described. Initially, the controller 30 connects the solution container 1 (port b) with the passage 5 (port a) by means of the switching valve 4, connects the passage 5 (port a) with the passage 10 (port b) by means of the switching valve 7, and connects the passage 12 (port a) with the passage 13 (port c) by means of switching valve 15, and activates the liquid-delivery pump 6 in such a manner as to deliver the liquid at a predetermined constant flow rate, in order to capture the target component contained in the solution in the solution container 1 by means of the absolvents in the trap column 8 and discard the solvent (mobile phase) in the solution. The liquid-delivery pump 6 draws the solution in the solution container 1 and introduces the solution to the trap column 8 through the passage 5 and the passage 10. Then, the target component in the solution is captured by the absolvents in the trap column 8. The mobile phase, from which the target component is removed, is discarded to the waste liquid port through the passage 12 and the passage 13.

When the predetermined amount of solution in the solution container 1 is supplied to the trap column 8, or when the solution in the solution container 1 is supplied to the trap column 8 for a predetermined period of time, the controller 30 subsequently switches the ports of the switching valve 4 in such a manner as to connect the pure water container 2 (port c) with the passage 5 (port a). Then, the liquid-delivery pump 6 draws the pure water in the pure water container 2 and introduces the pure water to the trap column 8. This removes undesirable water-soluble substances, such as salts attached to the absolvents during the aforementioned capture of the target component, from the trap column 8. The supply of the pure water enables the substitution of the water for the mobile phase accumulated in the trap column 8 immediately before the supply of the pure water, and the trap column 8 is in a state of being filled with the water. The target component captured by the absolvents is hardly eluted to the water due to strong absorption action, so that, at this time point, the target component is left in a state of being captured in the trap column 8.

Subsequently, the controller 30 transfers the fractional head 16 to above the predetermined infusion container 21 designated in advance and moves the fractional head 16 down by means of the XYZ drive mechanism 29 (FIG. 3B). This allows the sample introducing tube 17 to be inserted into the interior of the infusion container body 19 through the cushion admitting concave part 42 and the hole provided in the center of the cushion 43. The exhaust sealing tube 18 also descends and presses the cushion 43 provided on the lid 20, thereby hermetically sealing space between the exhaust sealing tube 18 and the infusion container 21.

Furthermore, the controller 30 instructs the target temperature to the temperature adjusting part 28 for the target temperature, which starts heating the temperature adjusting block 27 so that the infusion container 21 is warmed. The target temperature, for example, only needs to be approximately equal to or slightly higher than the boiling point of the dichloromethane used for the eluting solvent of the target component, which approximately ranges from 40 to 45 degrees Celsius. Subsequently, the controller 30 switches the ports of the switching valve 4 in such a manner as to connect the eluting solvent container 3 (port d) with the passage 5 (port a). Accordingly, the liquid-delivery pump 6 draws the dichloromethane in the eluting solvent container 3 and starts introducing the dichloromethane to the trap column 8.

When the dichloromethane is introduced to the trap column 8, the dichloromethane is hardly mixed with the water existing in the trap column 8, and the interface between the dichloromethane and the water gradually ascends. That is, the dichloromethane is gradually accumulated on the bottom of the trap column 8 while the water is pushed upward due to the introduction of the dichloromethane. In contrast, the water pushed upward leaks out from the outlet end of the upper end of the trap column 8 and leads from the passage 13 to the waste liquid port through the switching valve 15. In contrast with the water, the dichloromethane has a strong elution force, so that the target component captured by the trap column 8 dissolves into the dichloromethane accumulated in the trap column 8.

When the predetermined amount of dichloromethane in the eluting solvent container 3 is supplied to the trap column 8, or when the dichloromethane in the eluting solvent container 3 is supplied to the trap column 8 for a predetermined period of time, and the water is completely eliminated from the trap column 8, the controller 30 switches the ports of the switching valve 15 from the passage 13 (port c) to the passage 14 (port b) and starts fractionating the target component. Meanwhile, the controller 30 causes the gas supply part 23 to start the supply of nitrogen gas (or other inert gas). The nebulizing gas delivered by the gas supply part 23 is introduced to the outer tube 41 of the sample introducing tube 17 through the passage 22 and ejected from the tip end of the outer tube 41. The solution delivered from the trap column 8, that is, the dichloromethane containing the target component, is dropped from the tip end of the inner tube 40 of the sample introducing tube 17 through the passage 12 and the passage 14. While being dropped, the solution is sheared by the flow of the nebulizing gas blown from its surroundings, turned to fine droplets, and dispersed around the surroundings.

The infusion container 21 is heated at a temperature approximately equal to the boiling point of the dichloromethane, by heat conduction from the temperature adjusting block 27, in which the heater 25 is provided as a heat source. Accordingly, when the fine droplets of the solution are attached to the wall surface of the inner circumference or the inner bottom of the infusion container 21, the solvent in the droplets (dichloromethane) immediately vaporizes, and the target component remains as a powder. Thus, the powdered target component is accumulated on the wall surface of the inner circumference or the inner bottom of the infusion container 21. Further, the nebulizing gas introduced in the infusion container 21 or the vaporized solvent is discharged to the outside of the infusion container 21 through the exhaust sealing tube 18.

When the aforementioned process is completed, the fractional head 16 is moved upward. Accordingly, the sample introducing tube 17 and the exhaust sealing tube 18 are integrally moved upward, whereas the cushion 43 is engaged by the engaging part 44 formed on the lateral surface of the inner circumference of the cushion admitting concave part 42 of the lid 20 in the infusion container 21 used in the present embodiment, which prevents the cushion 43 from moving upward, irrespective of the upward movement of the exhaust sealing tube 18. Consequently, even when the fractional head 16 is subsequently transferred to a position where the next infusion container is disposed, and the same process is carried out, this process is not hampered by the cushion of the previous infusion container.

Thus, the procedure of the gas-blowing vaporizing and drying process of the present embodiment, in which the preparative separation-purification device in FIG. 1 is used, has been described. Next, the modified example of the infusion container and the gas-blowing liquid sample infusing device of the present embodiment will be described referring to FIGS. 4A and 4B, FIG. 5 and FIGS. 6A, 6B and 6C.

Figure 4A:
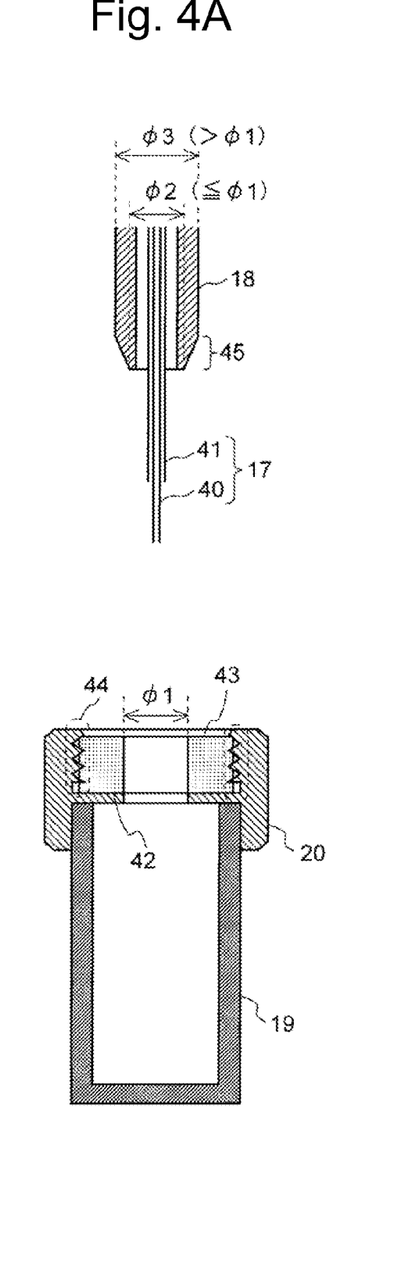
FIG. 4A is a diagram illustrating the dimensions of the exhaust sealing tube with respect to the diameter of a hole in the center of a doughnut-shaped cushion provided in a lid of the infusion container.
Figure 4B:
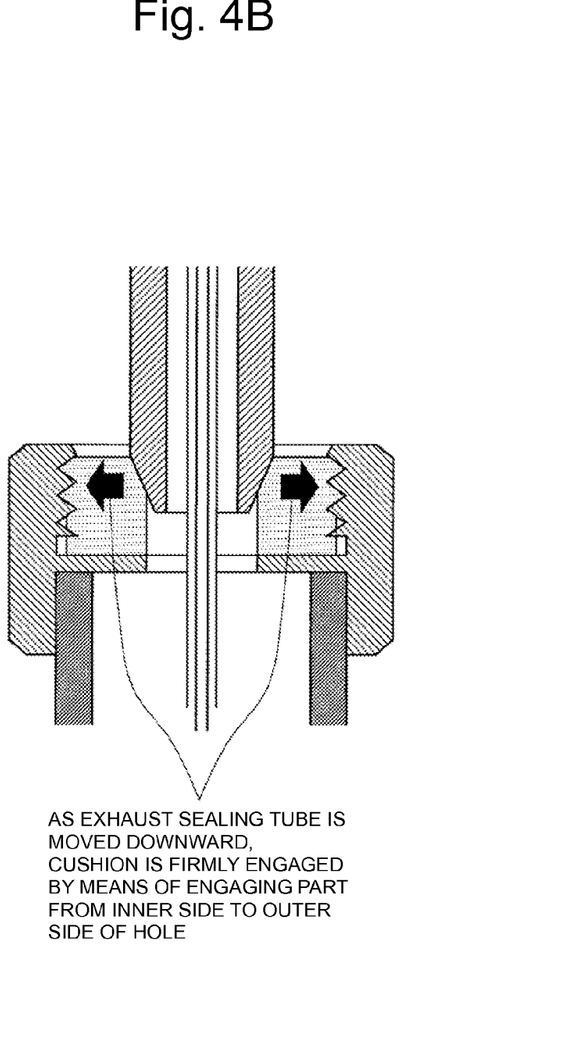
FIG. 4B is a diagram illustrating a state where the exhaust sealing tube is moved downward and inserted into the hole.

FIGS. 4A and 4B are schematic longitudinal cross-sectional diagrams illustrating the modified example of the exhaust sealing tube 18 of the gas-blowing liquid sample infusing device. The exhaust sealing tube 18 includes a tapered pointed part 45 on the end thereof. The pointed part 45 is designed in such a manner that the external diameter $\phi_2$ of the thinnest portion thereof is equal to or less than the diameter $\phi_1$ of the hole provided in the center of the cushion 43, and that the external diameter $\phi_3$ of the thickest portion thereof is larger than the diameter $\phi_1$ of the hole (FIG. 4A). Similar to the aforementioned gas-blowing vaporizing and drying process, when the exhaust sealing tube 18 is moved downward so as to cause the pointed part 45, whose sizes are designed in the aforementioned manner, to be inserted into the hole provided in the center of the cushion 43, so that the cushion 43 is pressed from the inner side to the outer side of the hole in accordance with the inclination of the pointed part 45 (FIG. 4B). Accordingly, the exhaust sealing tube 18 is hermetically sealed by the cushion 43, and the cushion 43 is pressed to the engaging part 44, deformed, and inserted into the engaging part 44. As the cushion 43 of the present embodiment, closed cell fluororubber sponge sheets having a hardness of 36 are used. When the exhaust sealing tube 18 is moved upward, the deformed cushion 43 does not immediately return to its original shape, and remains an inserted state into the engaging part 44 for a while (approximately several seconds). Accordingly, even when the exhaust sealing tube 18 is moved upward, upward movement of the cushion 43 is exceedingly restrained.

Figure 5:
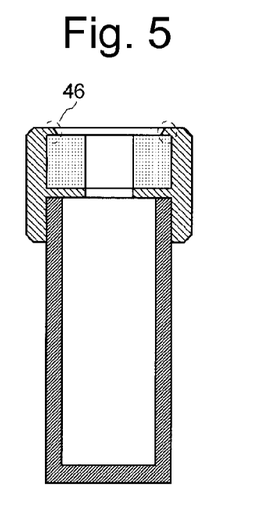
FIG. 5 is a schematic longitudinal cross-sectional diagram illustrating the modified example of the infusion container used in the gas-blowing liquid sample infusing device of the present embodiment.

FIG. 5 is a schematic longitudinal cross-sectional diagram illustrating the modified example of the infusion container 21. This infusion container 21 is provided with barbs 46 on the lateral surface of the inner circumference of the cushion admitting concave part 42 of the lid 20 as an engaging member. When the exhaust sealing tube 18 is moved downward, adhered to the cushion 43, and moved upward afterwards, the cushion 43 is engaged by the barbs 46, which prevents the cushion 43 from moving upward together with the exhaust sealing tube 18.

Figure 6A:
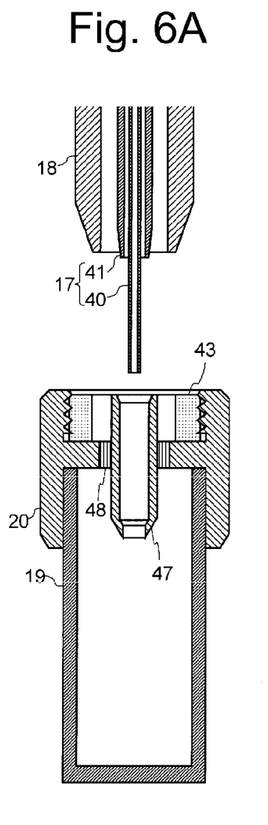
FIGS. 6A and 6B are schematic longitudinal cross-sectional diagrams and FIG. 6C is a schematic partial cross-sectional diagram each of which illustrates another modified example of the infusion container used in the gas-blowing liquid sample infusing device of the present embodiment.
Figure 6B:
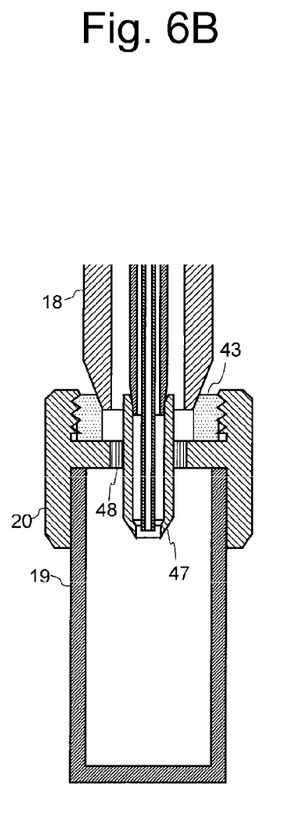
Figure 6C:
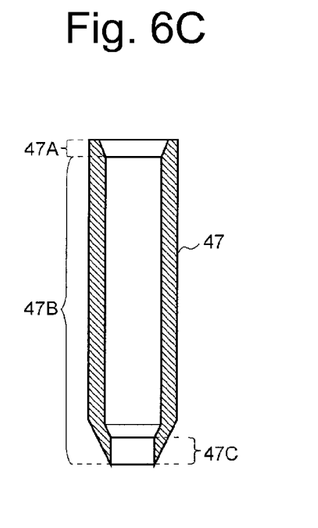

FIGS. 6A, 6B and 6C illustrate another modified example of the infusion container 21. The lid 20 of this infusion container 21 further includes a protruding part sleeve tube 47 and a filter 48 in addition to the structure in FIGS. 4A and 4B (FIG. 6A). The protruding part sleeve tube 47 includes a joining part 47A that hermetically joins the end of the outer tube 41 of the sample introducing tube 17 on the inlet side thereof and a sleeve part 47B that covers the protruding part of the inner tube 40 of the sample introducing tube 17 on the outlet side thereof (FIG. 6C).

Both of the outer circumference of the end of the outer tube 41 and the inner circumference of the joining part 47A are inclined in such a manner as to taper off as they advance downward. The inclination angle (an angle formed between the center axis of the joining part 47A and the inclined plane) of the joining part 47A is wider than the inclination angle (an angle formed between the center axis of the outer tube 41 and the inclined plane) of the outer tube 41. Accordingly, as the sample introducing tube 17 is moved downward, the outer tube 41 (and the inner tube 40) is introduced to the center of the joining part 47A, thereby hermetically sealing the space therebetween.

The sleeve part 47B is designed such that the inner diameter of an end part 47C on the outlet side is thinner than the inner diameter on the inlet side, and the length of the sleeve part 47B is adjusted in such a manner as to prevent the end of the inner tube 40 from protruding from the end part 47C when the outer tube 41 is joined with the joining part 47A (FIG. 6B). This prevents the droplets or the powder scattered in the interior of the infusion container body 19 from attaching to the protruding part of the inner tube 40. Furthermore, the outer tube 41 is not introduced to the interior of the infusion container body 19, so that the droplets and the powder are not attached to the outer tube 41. That is, when a different liquid sample is infused into the next infusion container, the occurrence of contamination due to attachment of the droplets and the powder to the sample introducing tube 17 can be prevented. It is preferable that the sleeve part 47B be adjusted to a length in which the tip end of the inner tube 40 is disposed within the tip end part 47C. Accordingly, the nebulizing gas passing through the outer tube 41 and flowing through the protruding part sleeve tube 47 converges at the end of the inner tube 40, so that the shearing of the solution dropped from the inner tube 40 is facilitated. The filter 48 serves to prevent the powdered solute in the interior of the infusion container body 19 from flowing out to the exhaust sealing tube 18 when the gas or the like is evacuated from the interior of the infusion container body 19 through the exhaust sealing tube 18.

As described above, the infusion container and the gas-blowing liquid sample infusing device according to the present invention have been described with reference to the embodiments, but needless to say, changes and modifications can be appropriately applied within the scope of the gist of the present invention.

REFERENCE SIGNS LIST

1 . . . Solution Container
2 . . . Pure Water Container
3 . . . Eluting Solvent Container
4 . . . Switching Valve
5, 10, 11, 12, 13, 14, 22 . . . Passage
6 . . . Liquid-Delivery Pump
7 . . . Switching Valve
8 . . . Trap Column
9 . . . Column Rack
15 . . . Switching Valve
16 . . . Fractional Head
17 . . . Sample Introducing Tube
40 . . . Inner Tube
41 . . . Outer Tube
18 . . . Exhaust Sealing Tube
19 . . . Infusion Container Body (Sample Container)
20 . . . Lid (Engaging Member)
21 . . . Infusion Container
23 . . . Gas Supply Part
23A . . . Proportional Valve
23B . . . Gas Cylinder
24 . . . Container Rack
25 . . . Heater
26 . . . Temperature Sensor
27 . . . Temperature Adjusting Block
28 . . . Temperature Adjusting Part
29 . . . XYZ Drive Mechanism
30 . . . Controller
31 . . . Operating Part
42 . . . Cushion Admitting Concave Part
43 . . . Cushion (Cushion Member)
44 . . . Engaging Part
45 . . . Pointed Part
46 . . . Barb
47 . . . Protruding Part Sleeve Tube
47A . . . Joining Part
47B . . . Sleeve Part
47C . . . End Part
48 . . . Filter

The invention claimed is:

1. An infusion container used for a gas-blowing liquid sample infusing device which includes a sample introducing tube for nebulizing and supplying a liquid sample and an exhaust sealing tube provided on a circumference of the sample introducing tube, where the sample introducing tube is made from a liquid-sample inner tube and a nebulizing-gas outer tube, the infusion container comprising:
a container body having an opening on an upper part;
a lid part configured to be mounted on the opening;
a cushion admitting concave part provided in the lid and having an opening on an upper part and a hole, for allowing the sample introducing tube to pass through on a bottom part;
an annular cushion member configured to be admitted in the cushion admitting concave part, the annular cushion member having a contact surface for contacting a lower end of the exhaust sealing tube; and
an engaging part provided on a surface of an inner circumference of the cushion admitting concave part and configured to prevent an upward movement of the cushion member.

2. The infusion container for the gas-blowing liquid sample infusing device, according to claim 1,
wherein the engaging part is made from screw-shaped notches provided on the surface of the inner circumference.

3. The infusion container for the gas-blowing liquid sample infusing device, according to claim 2,
wherein the engaging part is made from barbs provided on the surface of the inner circumference.

4. A gas-blowing liquid sample infusing device that nebulizes and supplies a liquid sample to an interior of a sample container having an opening on an upper part, comprising:
a sample introducing tube made from a liquid-sample inner tube that supplies the liquid sample and a nebulizing-gas outer tube that supplies gas for nebulizing the liquid sample;
an exhaust sealing tube provided on a circumference of the sample introducing tube;
an annular cushion member configured to be mounted on the opening, the annular cushion member having a through hole for allowing the sample introducing tube to pass through and a contact surface for contacting a lower end of the exhaust sealing tube; and
an engaging member configured to be mounted on the opening and configured to prevent an upward movement of the cushion member in a state where the cushion member is mounted on the opening.

5. The gas-blowing liquid sample infusing device according to claim 4,
wherein the engaging member is a lid of the sample container, and
wherein the lid includes a cushion admitting concave part configured to admit the cushion member and having an engaging part, formed on a surface of an inner circumference of the cushion admitting concave part, wherein the engaging part is configured to prevent the upward movement of the cushion member.

6. The gas-blowing liquid sample infusing device according to claim 5,
wherein a tapered pointed part is provided at a tip end of the exhaust sealing tube, and
wherein an external diameter of the thinnest portion of the tapered pointed part is equal to or less than a diameter of the through hole, and an external diameter of the thickest portion of the tapered pointed part is larger than the diameter of the through hole.

7. The gas-blowing liquid sample infusing device according to claim 5, wherein the engaging part is made from screw-threads formed on the surface of the inner circumference.

8. The gas-blowing liquid sample infusing device according to claim 5,
wherein the engaging part is made from barbs provided on the surface of the inner circumference.

9. The gas-blowing liquid sample infusing device according to claim 6,
wherein the engaging part is made from screw-threads formed on the surface of the inner circumference.

10. The gas-blowing liquid sample infusing device according to claim 6,
wherein the engaging part is made from barbs provided on the surface of the inner circumference.

* * * * *